(12) United States Patent
Hawkins

(10) Patent No.: US 7,288,115 B2
(45) Date of Patent: Oct. 30, 2007

(54) MULTIPART COMPONENT FOR AN ORTHOPAEDIC IMPLANT

(75) Inventor: Michael E. Hawkins, Columbia City, IN (US)

(73) Assignee: Zimmer Technology, Inc., Chicago, IL (US)

( * ) Notice: Subject to any disclaimer, the term of this patent is extended or adjusted under 35 U.S.C. 154(b) by 417 days.

(21) Appl. No.: 10/751,087

(22) Filed: Jan. 2, 2004

(65) Prior Publication Data
US 2005/0149198 A1 Jul. 7, 2005

(51) Int. Cl.
A61F 2/38 (2006.01)
(52) U.S. Cl. .................................. 623/20.14
(58) Field of Classification Search ............ 623/11.11, 623/16.11, 18.11, 20.14, 20.15, 20.17, 20.21, 623/20.32, 20.33–20.36, 23.56, 23.58, 23.59
See application file for complete search history.

(56) References Cited

U.S. PATENT DOCUMENTS

| 4,016,606 | A | * | 4/1977 | Murray et al. ............ 623/20.21 |
| 4,207,627 | A | * | 6/1980 | Cloutier .................... 623/20.21 |
| 4,211,228 | A | * | 7/1980 | Cloutier ....................... 606/102 |
| 4,217,666 | A | * | 8/1980 | Averill ..................... 623/20.33 |
| 4,249,270 | A | | 2/1981 | Bahler et al. |
| 4,257,129 | A | * | 3/1981 | Volz .......................... 623/20.33 |
| 4,711,639 | A | * | 12/1987 | Grundei .................... 623/20.33 |
| 4,714,474 | A | * | 12/1987 | Brooks et al. ........... 623/20.33 |
| 5,123,928 | A | | 6/1992 | Moser |
| 5,766,257 | A | * | 6/1998 | Goodman et al. ........ 623/20.21 |
| 6,126,692 | A | * | 10/2000 | Robie et al. .............. 623/20.32 |
| 6,365,089 | B1 | * | 4/2002 | Krebs et al. ................. 264/485 |
| 6,432,349 | B1 | * | 8/2002 | Pletcher et al. ............. 264/479 |
| 6,620,198 | B2 | * | 9/2003 | Burstein et al. .......... 623/20.28 |
| 6,660,039 | B1 | * | 12/2003 | Evans et al. .............. 623/20.29 |
| 6,709,461 | B2 | * | 3/2004 | O'Neil et al. ............. 623/20.33 |
| 6,794,423 | B1 | * | 9/2004 | Li ................................ 522/157 |
| 2004/0002767 | A1 | | 1/2004 | Wyss |

FOREIGN PATENT DOCUMENTS

EP 1132063 9/2001
EP 1269940 1/2003

* cited by examiner

Primary Examiner—Anuradha Ramana
(74) Attorney, Agent, or Firm—Baker & Daniels LLP

(57) ABSTRACT

The present invention provides an implant for replacing an articulating bone end adjacent a skeletal joint. The implant includes individual subcomponents having different physical and/or mechanical properties joined together into a multipart implant component.

13 Claims, 2 Drawing Sheets

MULTIPART COMPONENT FOR AN ORTHOPAEDIC IMPLANT

FIELD OF THE INVENTION

The present invention relates to orthopaedic implants. More particularly, the present invention relates to articular bearing surfaces for orthopaedic implants.

BACKGROUND

Joint replacement implants have been developed for the major skeletal joints of the human body. The implants are used to replace diseased or traumatized joint surfaces to reduce pain and restore function. Such implants typically include opposing joint components wherein each component defines an articulating bearing surface. For example, an orthopaedic knee implant may include a femoral component for replacing the femoral articulating condyles and a tibial component for replacing the tibial articulating surface. The femoral component typically includes a metallic articulating bearing surface which glides and pivots on a non-metallic articulating bearing surface of the tibial component. For example, many knee implants comprise a femoral component made of a metal such as Ti-6Al-4V alloy or Cobalt-Chromium-Molybdenum alloy and a tibial bearing surface made of ultra high molecular weight polyethylene (UHMWPE). Whatever type of implant or materials are involved, it is generally desirable for orthopaedic bearing surfaces to exhibit low wear. Furthermore, the bearing surfaces have minimum strength and toughness requirements. These bearing surfaces primarily experience compressive loading and sliding wear.

In addition to providing for articulation, the implant components may include constraint mechanisms to provide some degree of constraint to the motion permitted between the components. These constraint mechanisms may replace or augment natural constraint in the joint such as that provided by tendons and ligaments crossing the joint. These constraint mechanisms may provide the function of missing or damaged natural constraints. For example, in a posterior stabilized knee prosthesis, the tibial articular surface may include a post that projects upwardly to interact with a cam and box formed on the femoral component to limit rotation, varus/valgus tipping, anterior/posterior translation, posterior rollback, and/or other parameters of knee motion. Such constraint mechanisms may see significant bending, shear, and even impact loads within the limits of normal operation. Therefore, it is generally desirable for the constraint mechanism components to have high strength and toughness. Furthermore, the constraint mechanisms have limits to the permissible wear that can occur between contacting surfaces.

It may be the case that a particular type of implant has an articular bearing surface for which low wear is of prime importance and which further includes a constraint mechanism portion for which strength and toughness are of prime importance. For example, in a posterior stabilized knee, it is desirable for the articular condyles to exhibit low wear and the tibial post to exhibit high strength and toughness.

SUMMARY

The present invention provides an implant for replacing an articulating bone end adjacent a skeletal joint.

In one aspect of the invention, an implant includes first and second components to replace a portion of each of a pair of opposed articulating bone ends. The second component has means for low friction articulation with the first component and means for engaging the first component to constrain the motion between the components. The means for low friction articulation includes a first material exhibiting low wear and having a predetermined toughness value. The means for engaging includes a second material having a predetermined toughness value higher than the means for low friction articulation.

In another aspect of the invention, a tibial bearing component for replacing a portion of the proximal tibial surface of a knee joint includes a first portion having a bearing surface. The bearing surface has a region exhibiting low wear and has a first predetermined toughness value. The tibial bearing component includes a second portion having an intercondylar region. The intercondylar region has a region having a second predetermined toughness value that is greater than the first predetermined toughness value. The first and second portions are joined together to form a tibial bearing component.

In another aspect of the invention, a tibial implant for a knee joint includes first and second bearing portions. Each of the first and second bearing portions includes an articular surface having a first predetermined toughness value. An intercondylar portion is interposed between the first and second bearing portions. The intercondylar portion has a second predetermined toughness value greater then the first predetermined toughness value of the bearing portions.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DESCRIPTION OF THE ILLUSTRATED EMBODIMENTS

The articulating joint construction of the present invention may be used in implants for any articulating joint, including for example, the articulating joints of the skeletal system. For example, the construction may be incorporated into implants for the hip, knee, shoulder, vertebrae, elbow, wrist, ankle, jaw, and digits. In the illustrative embodiments, a tibial knee component is depicted, although it will be understood by those skilled in the art that this invention may be suitable for other applications as well.

Figure 1:
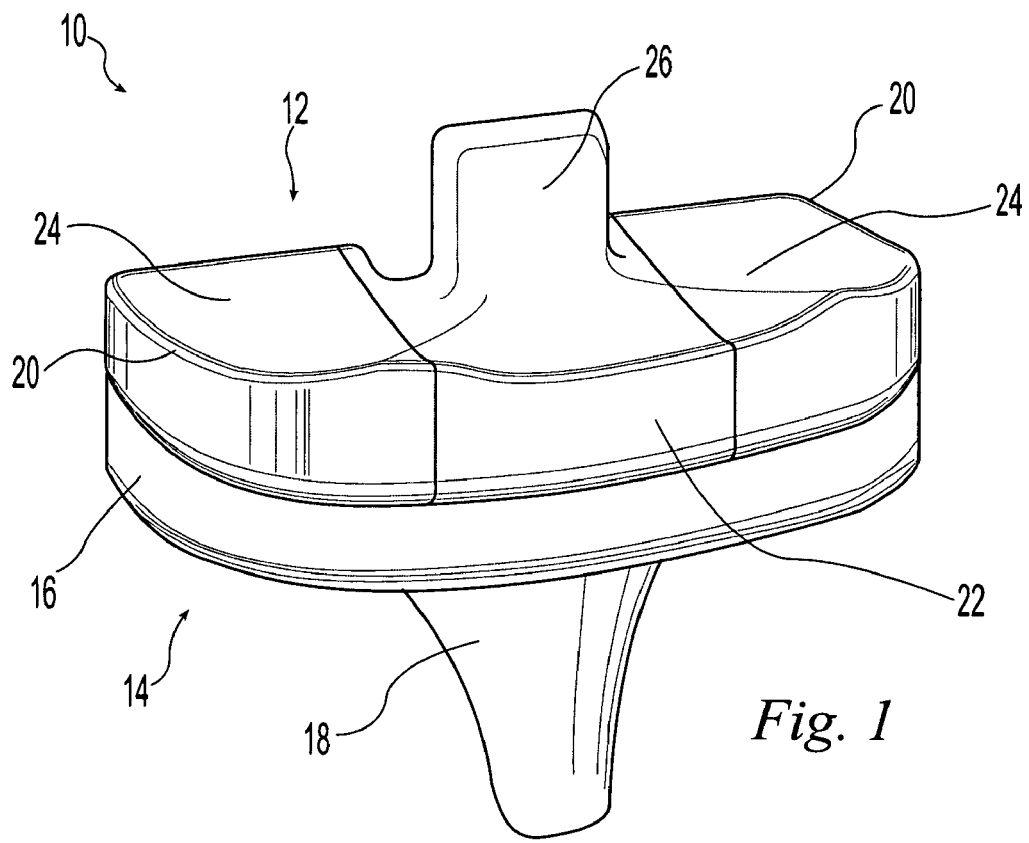
FIG. 1 is a perspective view of an implant component according to the present invention having a multipart bearing component and a support component.
Figure 2:
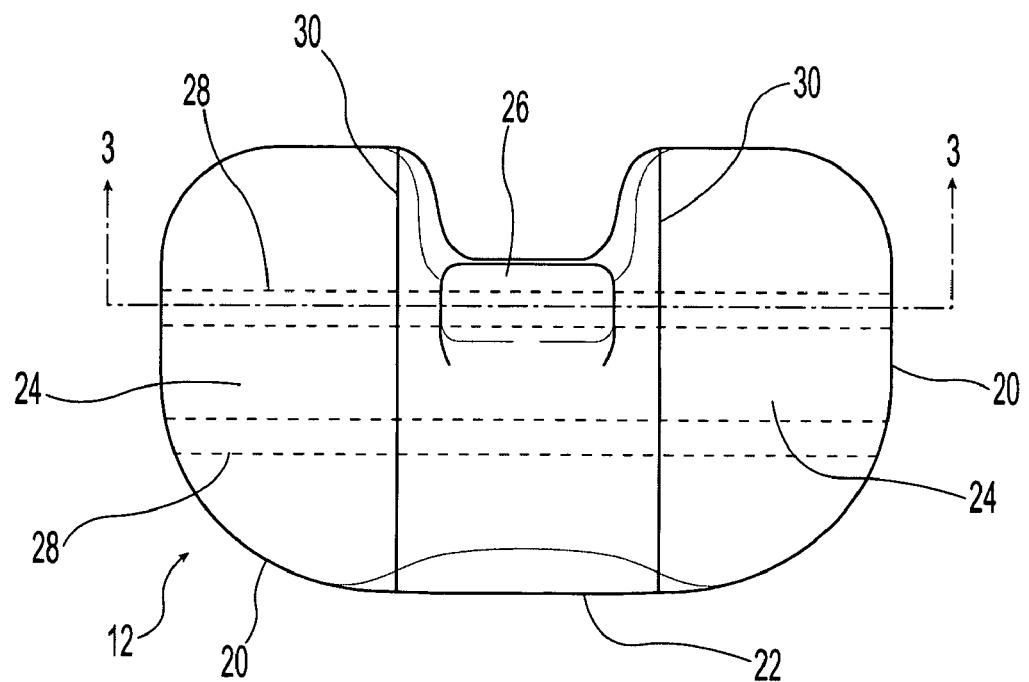
FIG. 2 is a top plan view of the implant of FIG. 1.
Figure 3:
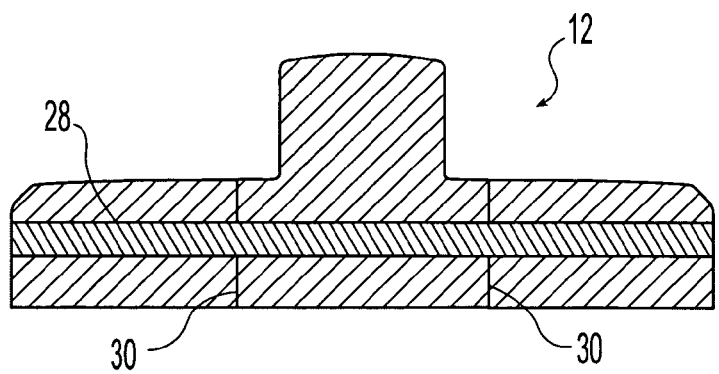
FIG. 3 is a sectional view of the bearing component of the implant of FIG. 1 taken along line 3-3.

FIGS. 1-3 illustrate a tibial knee component 10 including an articular bearing insert 12 and a supporting tray 14. The tray 14 includes an upper portion 16 for receiving the bearing insert 12 and a stem extension 18 for insertion into the tibial bone to hold the tray 14 in place. The bearing insert 12 is divided into three discrete portions including two outer condylar components 20 and an intercondylar component 22. The condylar components 20 each include an articular surface 24 for low friction articulation with a femoral component (not shown). The articular surfaces 24 may be made of a variety of bearing materials including polymers, ceramics, metals, and other suitable materials. For example, they may be made of UHMWPE. It is desirable to minimize the wear between the articular surfaces 24 and the femoral component. To this end, the articular surfaces 24 may be made of relatively hard and/or brittle materials that exhibit low wear. Examples include highly crosslinked UHMWPE and/or zirconia and alumina ceramics. These materials easily meet the strength requirements for the articular surfaces 24 since the articular surfaces 24 are primarily loaded in compression. For example, it is known to use chemicals and/or radiation to highly crosslink UHMWPE to improve its wear properties. Various forms of irradiation may be used including gamma and electron beam irradiation. For example, it is known to produce highly crosslinked UHMWPE by irradiation with doses greater than 6 Mrad. In particular, radiation doses from 6.5 to 11 Mrad have been used to highly crosslink UHMWPE to achieve dramatic increases in wear characteristics. Conversely, UHMPE medical devices are commonly irradiated to sterilize them. However, the irradiation dose for sterilization is approximately in the range of 2.5-3.7 Mrad. This dose range may result in lightly cross linked UHMWPE, but it does not result in an appreciable improvement in wear characteristics. Also, non-ionizing radiation, ethylene oxide gas, and other non-crosslinking forms of sterilization may be used that result in non-crosslinked polyethylene. The degree of crosslinking may be described in terms of the average molecular weight between crosslinks. For UHMWPE that has been gamma irradiated at low dose for sterilization purposes, the molecular weight between crosslinks is on the order of 8800 grams per mole. For highly crosslinked polyethylene, the average molecular weight between crosslinks is on the order of 3000-4000 grams per mole. Another way to describe the degree of crosslinking is in terms of swell ratio. In this measurement, a sample of the polyethylene is exposed to a solvent. As the sample absorbs the solvent, it swells. Crosslinks inhibit the swelling. Thus the ratio of the size of the swollen sample to its original size yields a measure of the degree of crosslinking. For UHMWPE that has been gamma irradiated at low dose for sterilization purposes, the swell ratio is on the order of about 3.68. For highly crosslinked polyethylene, the swell ratio is on the order of about 2.3.

The intercondylar component 22 includes a tibial eminence 26 for engaging a box and/or cam formed on the femoral component to constrain the amount of relative motion permitted between the femoral and tibial 10 components. The tibial eminence 26 is subjected to a combination of loads including shear, bending, and impacts. Therefore, it is desirable for the tibial eminence 26 to be made of a material that is relatively tough and impact resistant. The eminence may be made of a variety of materials including UHMWPE, poly(ketone) polymers such as polyetheretherketone (PEEK), poly(amides), metals, and other suitable materials. Thus, it may be the case that the condylar components 20 and intercondylar component 22 are made from materials having different properties tailored to the expected loading of the different components. For example, the condylar components 20 may be made of materials that exhibit relatively low wear. This wear is typically quantified by measuring the weight loss exhibited by articulating components. The intercondylar components may be made of materials that exhibit relatively high toughness. Toughness may be described as the amount of energy required to cause a material to fail. One measure of toughness is fracture impact toughness measured by determining the amount of energy required to break notched samples with a calibrated pendulum. Tensile failure toughness can be gauged by measuring the area under a load/displacement curve.

The different properties may result from using the same base material but processing it differently. For example the condylar components 20 may be made of highly crosslinked UHMWPE while the intercondylar component 22 may be made of lightly or non-crosslinked UHMWPE. Similarly, the condylar components 20 and intercondylar component 22 may be made of the same metals but with different processing; e.g. differently annealed, work hardened, ion implanted, shot peened, or otherwise treated to produce one metal sample optimized for strength and another metal sample optimized for low wear articulation. Also, similarly, the condylar components 20 and intercondylar component 22 may be made of the same ceramic constituents but with different processing; e.g. differently process time, temperature, pressure, particle size, etc. to produce one ceramic sample optimized for strength and another ceramic sample optimized for low wear articulation.

The different properties may result from using different materials of the same class such as different polymers, different metals, different ceramics, or different materials from another suitable class of materials. For example, the condylar components 20 and intercondylar component 22 may be made of different polymers such as UHMWPE and PEEK respectively or different ceramics such as alumina and zirconia respectively.

Finally, the different properties may result from using materials from different classes. For example, the condylar components 20 and intercondylar component 22 may be made of polymers and metals respectively, polymers and ceramics respectively, ceramics and metals respectively, or other combinations.

Figure 4:
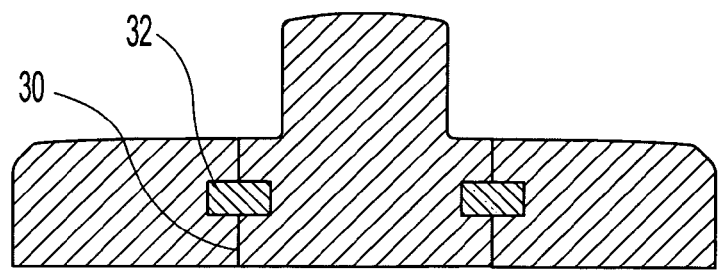
FIG. 4 is a sectional view similar to FIG. 3 showing an alternate arrangement for assembling the multipart bearing component.

The condylar components 20 and intercondylar component 22 may be joined together to form the tibial bearing insert 12 in a variety of ways. The components may be provided as a modular kit of parts that are joined together intraoperatively by the surgical staff to permit customizing the implant to a particular patients needs. Alternatively, the components may be permanently joined together at the time of manufacturing and supplied as a one piece tibial bearing insert 12. For example, the components may be permanently joined by bonding, by press fitting, or by molding them together in an interdigitating manner. Alternatively, the components may be press fit into the tray 14 to keep them in their proper relative positions. Alternatively, the components may be joined by mechanical fasteners. The tray may be omitted and the tibial bearing insert 12 configured to be placed directly on the tibial bone. For example, in the illustrative embodiment of FIGS. 1-3, the condylar components 20 and intercondylar component 22 are joined together with pins 28 press fit into the components perpendicular to the junction 30 between the components. A variation on this method is shown in FIG. 4 in which pins or splines 32 are pressed into the components parallel to the junction 30 between them.

Figure 5:
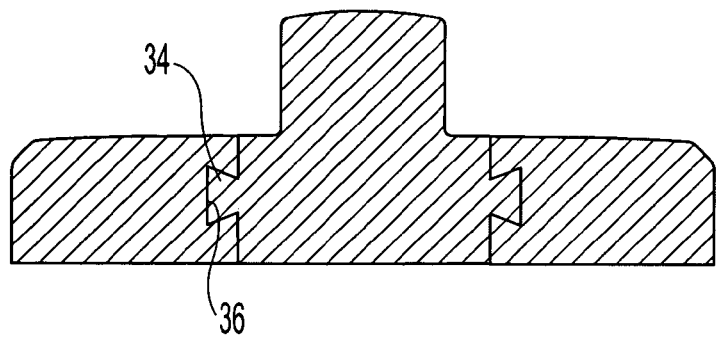
FIG. 5 is a sectional view similar to FIG. 3 showing an alternate arrangement for assembling the multipart bearing component.

FIG. 5 depicts a variation in which the intercondylar component 22 includes dovetail projections 34 and the condylar components include dovetail slots 36. The condylar components 20 and intercondylar component 22 are joined together by engaging the dovetail projections 34 with the dovetail slots 36.

Figure 6:
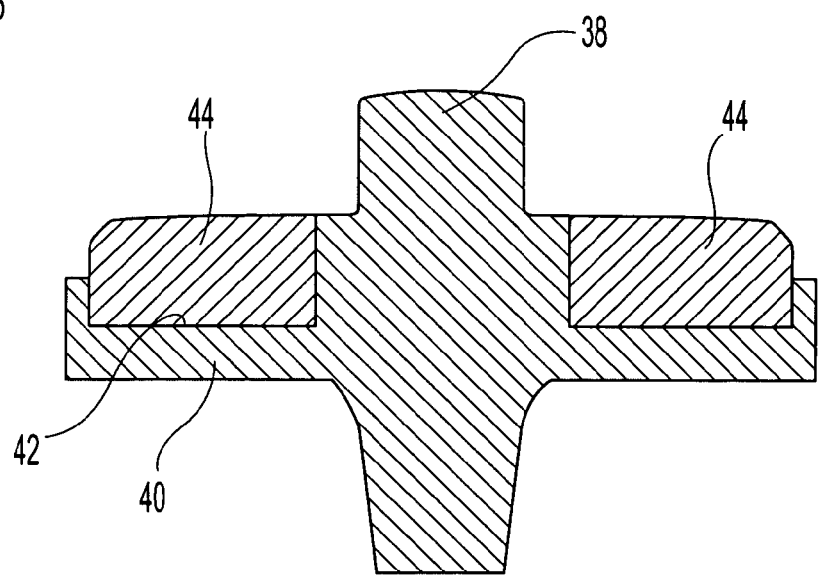
FIG. 6 is a sectional view similar to FIG. 3 showing an alternate arrangement for assembling the multipart bearing component.

FIG. 6 depicts an illustrative embodiment in which the intercondylar component 38 includes the tibial tray 40 as a unitary extension. The tray includes a support surface 42 for receiving the condylar portions 44.

It will be understood by those skilled in the art that the foregoing has described illustrative embodiments of the present invention and that variations may be made to these embodiments without departing from the spirit and scope of the invention defined by the appended claims.

What is claimed is:

1. A tibial knee implant for replacing a portion of the proximal tibial surface of a knee joint, the tibial knee implant being engageable with a femoral knee implant, the tibial knee implant comprising:
   a first articular bearing component;
   a second articular bearing component, the first and second articular bearing components comprising a first material exhibiting low wear and have a predetermined toughness value;
   an intercondylar component including an upwardly projecting intercondylar post engageable with the femoral knee implant to constrain the amount of relative motion permitted between the femoral and tibial knee implants, the intercondylar component comprising a second material having a predetermined toughness value greater than the first material; and
   at least one pin, the first articular bearing component, the second articular bearing component, and the intercondylar component being joined together by the pin extending into each of the components.

2. The implant of claim 1 wherein the first and second materials comprise polymers.

3. The implant of claim 2 wherein the first material comprises crosslinked polyethylene and the second material comprises uncrosslinked polyethylene.

4. The implant of claim 1 wherein the first material comprises relatively highly crosslinked polyethylene and the second material comprises relatively lightly crosslinked polyethylene.

5. The implant of claim 1 wherein the first and second materials are different materials selected from the same class of materials.

6. The implant of claim 5 wherein the first material comprises polyethylene and the second material comprises a poly(ketone).

7. The implant of claim 1 wherein the first and second materials are selected from different classes of material.

8. The implant of claim 7 wherein the first material comprises a polymer and the second material comprises a metal.

9. The implant of claim 7 wherein the first material comprises a ceramic and the second material comprises a polymer.

10. The tibial knee implant of claim 1 wherein the first articular bearing component, the second articular bearing component, and the intercondylar component are provided in sets that can be selectively joined together intraoperatively.

11. The tibial knee implant of claim 1 wherein the first articular bearing component, the second articular bearing component, and the intercondylar component are permanently joined together at the time of manufacture.

12. The tibial knee implant of claim 1 wherein the intercondylar component comprises a unitary tray extending from the intercondylar eminence, the tray including a support surface for receiving the first and second articular bearing components.

13. The tibial knee implant of claim 1 wherein the first articular bearing component, the second articular bearing component, and the intercondylar component are joined together with the intercondylar component being interposed between the first and second articular bearing components, the pin extending transversely into each of the components.

* * * * *